United States Patent [19]

Martin

[11] Patent Number: 5,733,875
[45] Date of Patent: Mar. 31, 1998

[54] METHODS OF USING GDNF AS A NEUROPROTECTIVE AGENT

[75] Inventor: David Martin, Boulder, Colo.

[73] Assignee: Amgen Inc., Thousand Oaks, Calif.

[21] Appl. No.: 446,383

[22] Filed: May 22, 1995

Related U.S. Application Data

[62] Division of Ser. No. 340,821, Nov. 15, 1994, abandoned.

[51] Int. Cl.$^6$ .............................................. A61K 38/17
[52] U.S. Cl. .............................. 514/12; 514/2; 530/350
[58] Field of Search .......................... 514/2, 12; 530/350; 435/69.1

[56] References Cited

FOREIGN PATENT DOCUMENTS

WO 93/06116  4/1993  WIPO.
WO 95/26408  10/1995  WIPO.

OTHER PUBLICATIONS

Altar et al. (1992), 'Brain–derived neuotrophic factor augments rotational behavior and nigrostriatal dopamine turnover in vivo', *Proc. Natl. Acad. Sci. U.S.A.* 89:11347–11351.
Ben–Ari et al. (1981), 'Electrographic, Clinical and Pathological Alterations Following Systemic Administration of Kainic Acid, Bicuculline or Pentetrazole: Metabolic Mapping Using the Deoxyglucose Method with Special Reference to the Pathology of Epilepsy', *Neurosci.* 6(7):1361–1391.
Ben–Ari (1985), 'Limbic Seizure and Brain Damage Produced by Kainic Acid: Mechanisms and Relevance to Human Temporal Lobe Epilepsy', *Neurosci.* 14(2):375–403.
Berlove et al. (1991), Basic Fibroblast Growth Factor (bFGF) Protects Against Ischemic Neuronal Death In Vivo', *Soc. Neurosci. Abstr.* 17:1267; abstract No. 501.13.
Cheng et al. (1991), 'NGF and bFGF Protect Rat Hippocampal and Human cortical Neurons against Hypoglycemic Damage by Stabilizing Calcium Homeostasis', *Neuron* 7:1031–1041.
Dingledine et al. (1988), 'Amino Acid Receptors and Uptake Systems in the Mamalian Central Nervous System', *Neurobiology* 4:1–96.
Ernfors et al. (1991), 'Increased Levels of Messenger RNAs for Neutrotrophic Factors in the Brain during Kindling Epileptogenesis', *Neuron* 7:165–176.
Follesa et al. (1994), 'Regional and Temporal Pattern of Expression of Nerve Growth Factor and Basic Fibroblast Growth Factor mRNA in Rat Brain Following Electroconvulsive Shock', *Exp. Neurol.* 127:37–44.
Gall et al. (1991), 'Kainic acid–induced seizures stimulates increased expression of nerve growth factor mRNA in rat hippocampus', *Mol. Brain Res.* 9:113–123.
Hajnal et al. (1992), 'Feeding Disturbances and EEG Activity Changes After Amygdlaoid Kainate Lesions in the Rat', *Brain Res. Bull.* 29:209–916.

Hefti et al. (1989), 'Function of Neurotrophic Factors in the Adult and Aging Brain and Their Possible Use in the Treatment of Neurodegenerative Diseases', *Neurobiol. Aging* 10:515–588.
Hudson et al. (1993), 'In Vivo Activity of GDNF, A Glial–Cell–Line–Derived Neurotrophic Factor, on the Rat Nigrostriatal Dopamine System', *Soc. Neurosci. Abstr.* 19:652; abstract No. 275.5.
Humpel et al (1994), 'Neurons of the hippocampal formation express glial cell line–derived neurotrophic factor messenger RNA in response to kainate–induced excitation', *Chem. Abstr.* 120:21, Abstract No. 262210k.
Humpel et al. (1994) 'Neurons of the Hippocampal Formation Express Glial Cell Line–Derived Neurotrophic Factor Messenger RNA in Response to Kainate–Induced Excitation', *Neurosci.* 59(4):791–795.
Lin et al. (1990), 'Isolation and Characterization of Ciliary Neurotrophic Factor from Rabbit Sciatic Nerves', *J. Biol. Chem.* 265(15):8942–8947.
Lin et al. (1993), 'GDNF: A Glial Cell Line–Derived Neurotrophic Factor for Midbrain Dopaminergic Neurons', *Science* 260:1130–1132.
Lin et al. (1994), 'Purification and Initial Characterization of Rat B49 Glial Cell Line–Derived Neurotrophic Factor', *J. Neurochem.* 63(2):758–768.
Lothman & Collins (1981), Kainic Acid Induced Limbic Seizures: Metabolic, Behavioral, Electroencephalographic and Neuropathological Correlates', *Brain Res.* 218:299–318.
Martin et al. (1994), 'rhGDNF Prevents Kainic Acid Induced Seizures and the Associated Neuronal Cell Death', *Soc. Neurosci. Abstr.* 20(1–2): p. 442.
Martin–Iverson et al. (1994), 'Brain–derived Neurotrophic Factor and Neurotrophic–3 Activate Striatal Dopamine and Serotonin Metabolism and Related Behaviors: Interactions with Amphetamine', *J. Neurosci.* 14(3):1262–1270.
Mattson et al. (1993), 'Growth Factors Protect Neurons Against Excitotoxic/Ischemic Damage by Stabilizing Calcium Homeostasis', *Stroke* 24(12):I136–I140.
McDonald et al. (1991), 'Expression and characterization of recombinant human ciliary neurotrophic factor from *Escherichia coli*', *Biochem. Biophys. Acta* 1090:70–80.

(List continued on next page.)

*Primary Examiner*—Paula K. Hutzell
*Assistant Examiner*—Stephen Gucker
*Attorney, Agent, or Firm*—Daniel R. Curry; Ron K. Levy; Steven M. Odre

[57] ABSTRACT

The present invention is directed to the use of glial–derived neurotrophic factor (GDNF) to inhibit or prevent seizure activity. The methods of the present invention are accomplished by administering GDNF to patients having or potentially having a neurodegenerative disorder such as epilepsy. Pharmaceutical compositions containing a therapeutically effective amount of GDNF in a pharmaceutically acceptable carrier are also provided.

11 Claims, 3 Drawing Sheets

OTHER PUBLICATIONS

Miller et al. (1994), 'Central Administration of rhGDNF Causes Augmentation of Dopaminergic Activity in vivo', *Soc. Neurosci. Abstr.* 20:535.7.

Nadler (1981), 'Kainic Acid as a Tool for the Study of Temporal Lobe Epilepsy', *Life Sci.* 29:2031–2042.

Nadler (1989), 'Seizures and Nueronal Cell Death in the Hippocampus', *The Hippocampus–New Vistas*, (Alan R. Liss) pp. 463–481.

Schaar et al. (1993), 'Regional and Cell–Specific Expression of GDNF in Rat Brain', *Exp. Neurol.* 124:368–371.

Shigeno et al. (1991), 'Amelioration of Delayed Neuronal Death in the Hippocampus by Nerve Growth Factor', *J. Neurosci.* 11(9):2914–2919.

Shimohama et al. (1993), 'Brain–derived neurotrophic factor pretreatment exerts a partially protective effect against glutamate–induced neurotoxicity in cultured rat cortical neurons', *Neurosci. Lett.* 164:55–58.

Stasheff et al. (1989), NMDA Antagonists differentiate Epileptogenesis from Seizure Expression in an in Vitro Model', *Science* 245:648–651.

Stromberg et al. (1993), 'Glail Cell Line–Derived Neurotrophic Factor is Expressed in the Developing but Not Adult Striatum and Stimulates Developing Dopamine Neurons in Vivo', *Exp. Neurol.* 124:401–412.

Tanaka et al. (1992), 'Experimental Complex Partial Seizures Induced by a Microinjection of Kainic Acid Into Limbic Structures', *Prog. Neurobiol.* 38:317–334.

Wong et al. (1986), 'The anticonvulsant MK–801 is a potent N–methyl–D–aspartate antagonist', *Proc. Natl. Acad. Sci. U.S.A.* 83:7104–7108.

Humpel et al., *Neuroscience*, vol. 59, pp. 791–795, 1994.

Schmidt–Kastner et al., *Mol. Brain Res.*, vol. 26, pp. 325–330, 1994.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 134 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..134
      ( D ) OTHER INFORMATION: /note= "Human GDNF"

( x i ) SEQUENCE DESCRIPTION: SEQ ID NO:1:

```
Ser Pro Asp Lys Gln Met Ala Val Leu Pro Arg Arg Glu Arg Asn Arg
 1               5                  10                  15

Gln Ala Ala Ala Ala Asn Pro Glu Asn Ser Arg Gly Lys Gly Arg Arg
                20                  25                  30

Gly Gln Arg Gly Lys Asn Arg Gly Cys Val Leu Thr Ala Ile His Leu
```

-continued

```
                    35                              40                              45

Asn  Val  Thr  Asp  Leu  Gly  Leu  Gly  Tyr  Glu  Thr  Lys  Glu  Glu  Leu  Ile
             50                       55                       60

Phe  Arg  Tyr  Cys  Ser  Gly  Ser  Cys  Asp  Ala  Ala  Glu  Thr  Thr  Tyr  Asp
        65                            70                       75                       80

Lys  Ile  Leu  Lys  Asn  Leu  Ser  Arg  Asn  Arg  Arg  Leu  Val  Ser  Asp  Lys
                            85                       90                            95

Val  Gly  Gln  Ala  Cys  Cys  Arg  Pro  Ile  Ala  Phe  Asp  Asp  Asp  Leu  Ser
                       100                      105                      110

Phe  Leu  Asp  Asp  Asn  Leu  Val  Tyr  His  Ile  Leu  Arg  Lys  His  Ser  Ala
                  115                           120                      125

Lys  Arg  Cys  Gly  Cys  Ile
             130
```

( 2 ) INFORMATION FOR SEQ ID NO:2:

( i ) SEQUENCE CHARACTERISTICS:
        ( A ) LENGTH: 134 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..134
        ( D ) OTHER INFORMATION: /note= "Rat GDNF"

( x i ) SEQUENCE DESCRIPTION: SEQ ID NO:2:

```
        Ser  Pro  Asp  Lys  Gln  Ala  Ala  Ala  Leu  Pro  Arg  Arg  Glu  Arg  Asn  Arg
        1                   5                        10                           15

Gln  Ala  Ala  Ala  Ala  Ser  Pro  Glu  Asn  Ser  Arg  Gly  Lys  Gly  Arg  Arg
                       20                       25                       30

Gly  Gln  Arg  Gly  Lys  Asn  Arg  Gly  Cys  Val  Leu  Thr  Ala  Ile  His  Leu
                  35                            40                       45

Asn  Val  Thr  Asp  Leu  Gly  Leu  Gly  Tyr  Glu  Thr  Lys  Glu  Glu  Leu  Ile
             50                       55                       60

Phe  Arg  Tyr  Cys  Ser  Gly  Ser  Cys  Glu  Ala  Ala  Glu  Thr  Met  Tyr  Asp
        65                            70                       75                       80

Lys  Ile  Leu  Lys  Asn  Leu  Ser  Arg  Ser  Arg  Arg  Leu  Thr  Ser  Asp  Lys
                            85                       90                            95

Val  Gly  Gln  Ala  Cys  Cys  Arg  Pro  Val  Ala  Phe  Asp  Asp  Asp  Leu  Ser
                       100                      105                      110

Phe  Leu  Asp  Asp  Ser  Leu  Val  Tyr  His  Ile  Leu  Arg  Lys  His  Ser  Ala
                  115                           120                      125

Lys  Arg  Cys  Gly  Cys  Ile
             130
```

METHODS OF USING GDNF AS A NEUROPROTECTIVE AGENT

The present application a divisional application of U.S. Ser. No. 08/340,821 filed on Nov. 15, 1994, now abandoned.

FIELD OF THE INVENTION

The present invention relates to the use of glial-derived neurotrophic factor (GDNF) as a neuroprotective agent, and more particularly as an anti-seizure therapeutic.

BACKGROUND OF THE INVENTION

Epilepsy is a common neurodegenerative disorder. Children and teens have the highest incidence of the disorder, with 75% of patients in this age group developing epilepsy before the age of 20. The disorder is characterized by chronic or recurrent seizures indicative of a central nervous system dysfunction that may be caused by a variety of different etiologic factors. For example, epilepsy has in part been ascribed to excessive release or impaired uptake of endogenous excitatory amino acids, such as glutamate, which can lead to neuronal damage, and necrosis (Sperk, Prog. in Neurobiol., 42:1–32 (1994); McNamara, J. Neurosci., 14:3413-1325 (1994)).

Seizures can be evoked in normal brain by treatments such as electroshock (Swinyard et al., J. Pharmac. Exp. Ther., 140:375–384 (1952)), kindling (Goddard et al., Exp. Neurol., 25:295 (1969)), or chemical convulsants (Nadler, Life Sci., 24:2031-2042 (1981); Ben-Ari et al., Neurosci., 6:1361-1391 (1981)). Seizure production via these methods and the subsequent brain damage initiate a complex cascade of regenerative and plastic changes including the expression of immediate early genes and growth factors in the hippocampus and in other brain regions of the adult rat (Sperk, Prog. in Neurobiol., 42:1–32 (1994)). Changes in the expression of nerve growth factor (NGF), basic fibroblast growth factor (bFGF) and brain derived neurotrophic factor (BDNF), contribute to plasticity of the injured brain in seizure models according to Gall et al., Mol. Brain Res., 9:113-123 (1991); Ernfors et al., Neuron, 7:165–176 (1991); and Follesa et al., Exp. Neurol., 127:37–44 (1994).

Systemic or intracranial administration of kainic acid to rats induces a syndrome characterized by an acute limbic status epilepticus and subsequent neuronal brain damage similar to that observed in temporal lobe epilepsy in humans. Thus, kainic acid is widely used as a tool to study temporal lobe epilepsy in experimental animals (Ben-Ari et al., Neurosci., 6:1361-1391 (1981); and Nadler, Life Sci., 24:2031-2042 (1981)).

The kainate receptor is one of three ionotropic glutamate receptors, the other two are named for their preferred agonists: NMDA (N-methyl-D-aspartate and AMPA ($\alpha$-amino-3-hydroxy-5-methyl-4-isoxazole propionate). The kainate and AMPA receptors are often referred to collectively as non-NMDA receptors. Non-NMDA receptors pass mainly monovalent cations and mediate fast excitatory synaptic transmission, and more recently have been shown to play an important role in the maintenance of certain plasticity processes (Miller, Neurosci., 14:477–479 (1991); and Muller et el., Science, 242:1694:1697 (1988)).

In a recent report, mRNA levels for a novel neurotrophic factor, glial derived neurotrophic factor (GDNF) were shown to increase in the adult hippocampus after seizures induced by kainic acid (Humpel et el., Neurosci., 59:791–795 (1994)). Glial-derived neurotrophic factor, a member of the transforming growth factor-$\beta$ (TGF-$\beta$) superfamily, has been cloned, expressed, and shown to manifest potent trophic activity for embryonic midbrain ventral mesencephalic dopaminergic neurons in vitro (Lin et al., Science, 260:1130–1132 (1993); and Lin et el., J. Neurochem., 63:758–768 (1994)). Recombinant human GDNF (rhGDNF) has also been demonstrated to induce sprouting of dopaminergic fibers in vivo (Hudson et al., Soc. Neurosci. Abstr., 19:652 (1993)), increase dopamine turnover in the substantia nigra of rats (Hudson et el., supra.; Miller et al., Soc. Neurosci. Abstr., 20:535.7 (1994)), protect neurons against 6-OHDA lesions, and augment growth and fiber formation of rat fetal transplants of nigral tissue in oculo (Stromberg et al., Exp. Neurol., 124:401–412 (1993)). Furthermore, in situ hybridization analysis has shown expression of GDNF mRNA in embryonic but not in normal adult brains, suggesting that rhGDNF may be a target-derived factor during development (Olson et el., Soc. Neurosci. Abstr., 19:652 (1993); and Stromberg et al., Exp. Neurol., 124:401–412 (1993)).

Epilepsy is often treated with drugs to prevent the occurrence of convulsive seizures. Of the patients who respond to such therapy, about 60% still experience seizures, although less frequently. Of the 40% of the patients who are treatable, many of these patients nevertheless experience severe side effects, for example, fatigue, drowsiness, and impotency that substantially affect a patient's quality of life. Accordingly, a need exists for alternative therapies that are effective and do not elicit such severe side effects. The present invention satisfies this need and provides related advantages as well.

SUMMARY OF THE INVENTION

The present invention is directed to the discovery that GDNF provides neuroprotection against disorders associated with seizures, such as epilepsy. Accordingly, the present invention provides methods for inhibiting seizures by administering GDNF to a patient in need of anti-seizure therapy in an amount sufficient to inhibit or prevent the onset of seizures.

Preferably, the GDNF is recombinantly produced and is administered in a pharmaceutically acceptable carrier. Therefore, the present invention further provides pharmaceutical compositions comprising a therapeutically effective amount of GDNF and a pharmaceutically acceptable carrier.

BRIEF DESCRIPTION OF THE DRAWINGS

(FIG. 2A): 7 days after kainate acid (12 mg/kg s.c.)+vehicle (2 μl icv). Note the necrosis of the CA1 pyramidal cells. (FIG. 2B): Normal rat sacrificed at the same time. (FIG. 2C): 7 days after kainate acid (12 mg/kg s.c.)+ rhGDNF (50 μg/2 μl, icv). Note the protection of the CA1 pyramidal cells.

DETAILED DESCRIPTION OF THE INVENTION

Figure 1A:
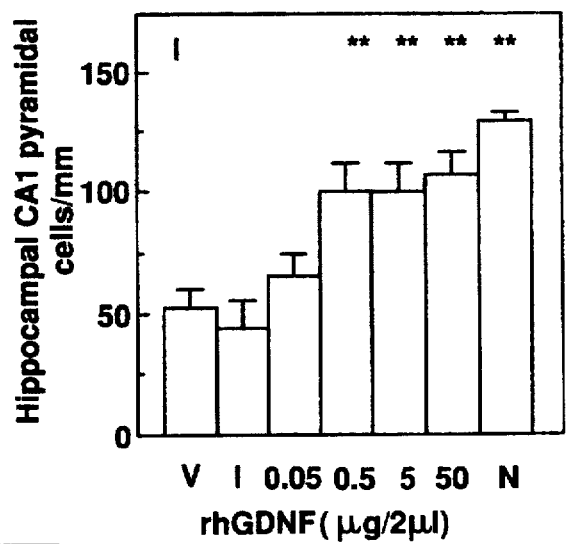
FIGS. 1A–1C shows that rhGDNF protects against kainic acid induced neuronal loss. Intraventricle GDNF (0.5, 5 50µg/2 µl) protects hippocampal CA1 (FIG. 1A), amygdala (FIG. 1B) and thalamic neurons (FIG. 1C) against kainic acid (12 mg/kg subcutaneous) induced lesions. Animals received either rhGDNF 0.05, 0.5, 5 or 50 µg/4 µl (C–F), respectively), inactive GDNF (B) or vehicle (A) 1 hour before Kainic acid administration. Group G represent normal animals that received no manipulations. Compared to the kainic acid/vehicle group, GDNF treated animals significantly increased neuronal survival in all regions examined. Neuron counts are the average±S.E.M. of 9–24 determinations. Significance of the difference between vehicle and rhGDNF was P<0.01 (**) and P<0.05 (*) using the Students t-test. Similarly, there was a significant difference (P<0.01) between the vehicle (A) and the no treatment (G) groups.

The present invention provides methods for inhibiting seizures in a patient by administering a therapeutically effective amount of GDNF, preferably recombinant human GDNF (rhGDNF).

In one embodiment of this invention, the preferred GDNF is the naturally occurring human protein. The naturally-occurring human protein is preferred for human therapy in part because it is believed to pose a lower risk of producing unforeseen and undesirable physiological side effects in patients treated therewith. However, to the extent that non-human GDNFs, such as rat GDNF, are substantially equivalent to human GDNFs and possess equivalent biological activity, they are considered to be within the scope of this invention as well.

For purposes herein, a protein is deemed to be "naturally-occurring" if it or a substantially equivalent protein can be found to exist normally in healthy humans. "Naturally-occurring" proteins specifically include forms of proteins found to exist in healthy humans that are partially truncated at the amino or carboxyl terminus of such proteins or that have amino acids that are deamidated or otherwise chemically modified. "Naturally-occurring" proteins may be obtained by recombinant DNA methods as well as by isolation from cells which ordinarily produce them. "Naturally-occurring" also encompasses proteins that contain or lack an $NH_2$-terminal methionyl group as consequence of expression $E.\ coli$.

"Substantially equivalent" as used throughout the specification and claims is defined to mean possessing a very high degree of amino acid residue homology (See generally M. Dayoff, Atlas of Protein Sequence and Structure, vol. 5, p. 124 (1972), National Biochemical Research Foundation, Washington, D.C., specifically incorporated herein by reference) as well as possessing comparable biological activity.

Particularly preferred GDNF of the present invention is the naturally-occurring protein that has been isolated from serum free growth conditioned medium of B49 gliobastoma cells as previously described in U.S. patent application No. 07/855,413 filed on Mar. 19, 1992, now abandoned (which is a continuation in part of U.S. patent application No. 07/788,423 filed on Nov. 6, 1991, now abandoned, which is a continuation in part of U.S. patent application No. 07/764, 685 filed on Sep. 20, 1991, now abandoned), which is specifically incorporated by reference. Other preferred forms of GDNF are also described in U.S. Ser. No. 07/855, 413, now abandoned.

For Example, human GDNF which has the amino acid sequence:

| Ser | Pro | Asp | Lys | Gln | Met | Ala | Val | Leu | Pro | Arg | Arg | Glu | Arg | Asn |
|-----|-----|-----|-----|-----|-----|-----|-----|-----|-----|-----|-----|-----|-----|-----|
| Arg | Gln | Ala | Ala | Ala | Ala | Asn | Pro | Glu | Asn | Ser | Arg | Gly | Lys | Gly |
| Arg | Arg | Gly | Gln | Arg | Gly | Lys | Asn | Arg | Gly | Cys | Val | Leu | Thr | Ala |
| Ile | His | Leu | Asn | Val | Thr | Asp | Leu | Gly | Leu | Gly | Tyr | Glu | Thr | Lys |
| Glu | Glu | Leu | Ile | Phe | Arg | Tyr | Cys | Ser | Gly | Ser | Cys | Asp | Ala | Ala |
| Glu | Thr | Thr | Tyr | Asp | Lys | Ile | Leu | Lys | Asn | Leu | Ser | Arg | Asn | Arg |
| Arg | Leu | Val | Ser | Asp | Lys | Val | Gly | Gln | Ala | Cys | Cys | Arg | Pro | Ile |
| Ala | Phe | Asp | Asp | Asp | Leu | Ser | Phe | Leu | Asp | Asp | Asn | Leu | Val | Tyr |
| His | Ile | Leu | Arg | Lys | His | Ser | Ala | Lys | Arg | Cys | Gly | Cys | Ile. | |

The nucleic acid sequences of the genes encoding human and rat GDNFs and the amino acid sequences of such proteins are also given in the U.S. Ser. No. 07/855,413 application now abandoned. The present invention encompasses non-glycosylated forms of GDNF as well as truncated forms of the naturally-occurring and recombinant GDNF proteins.

Modified forms of GDNF are also encompassed in the use of the present methods. For example, GDNF can be modified by attachment of one or more polyethylene glycol (PEG), other repeating polymeric moieties, or other side chains attached to the basic polypeptide backbone of GDNF. In a further embodiment, the amino acid sequence of the polypeptide chain can be modified, for example by the substitution, addition or deletion of one or more amino acids as long as the desired anti-convulsant activity of GDNF is not substantially impaired. Accordingly, the term "GDNF" is intended to encompass all forms of GDNF.

Methods for producing the various forms of GDNF are also disclosed in the U.S. Ser. No. 07/855,413 application now abandoned. One disclosed method consists of isolating GDNF from various sources, such as serum free medium of B49cell. A second disclosed method involves isolating the genes responsible for coding GDNF, cloning the gene in suitable vectors and cell types, and expressing the gene in order to produce the GDNF. The latter method, which is exemplary of recombinant DNA methods in general, is a preferred method of the present invention. Recombinant DNA methods are preferred in part because they are capable of achieving comparatively higher amounts of proteins with greater purity.

Preferably, the above described GDNF is produced by the aforementioned method in "substantially pure" form. By "substantially pure" it is meant that GDNF, in an unmodified form, has a comparatively high specific activity. It is to be recognized, however, that derivatives or modified forms of GDNF may have different specific activities.

Because it is possible that the anti-convulsive activity of GDNF is imparted by one or more discrete and separable portions of the protein, it is also envisioned that the method of the present invention could be practiced by administering a therapeutic composition whose active ingredient consists of that portion (or those portions) of GDNF which controls (or control) the anti-convulsive function.

In a preferred embodiment of the present invention, a pharmaceutical composition comprising GDNF is administered in an effective amount to patients for neuroprotection. For therapeutic applications, GDNF can be formulated in a pharmaceutically-acceptable carrier to produce pharmaceutical compositions. The term "pharmaceutically acceptable carrier" as used herein means a non-toxic, generally inert vehicle for the active agent, which does not adversely affect the agent or the patient to whom the composition is administered. Suitable vehicles or carriers can be found in standard pharmaceutical texts, for example, in *Remington's Pharmaceutical Sciences*, 16th ed., Mack Publishing Co., Easton, Pa. (1980), incorporated herein by reference. Such carriers include, for example, aqueous solutions such as bicarbonate buffers, phosphate buffers, Ringer's solution and physiological saline. In addition, the carrier can contain other pharmaceutically-acceptable excipients for modifying or maintaining the pH, osmolarity, viscosity, clarity, color, sterility, stability, rate of dissolution, or odor of the formulation.

The pharmaceutical compositions can be prepared by methods known in the art, including, by way of an example, the simple mixing of reagents. Those skilled in the art will know that the choice of the pharmaceutical carrier and the appropriate preparation of the composition depend on the intended use and mode of administration.

In one embodiment, it is envisioned that the carrier and GDNF as the active agent constitute a physiologically-compatible, slow-release formulation. It is possible to control the rate of release of the active agent(s) by proper choice of labile linking groups in the oligonucleotide, which would be known to those skilled in the art. The primary solvent in such a carrier can be either aqueous or non-aqueous in nature. In addition, the carrier can contain other pharmacologically-acceptable excipients for modifying or maintaining the pH, osmolarity, viscosity, clarity, color, sterility, stability, rate of dissolution, or odor of the formulation. Similarly, the carrier can contain still other pharmacologically-acceptable excipients for modifying or maintaining the stability, rate of dissolution, release, or absorption of the active agents. Such excipients are those substances usually and customarily employed to formulate dosages for parenteral administration in either unit dose or multi-dose form.

Once the pharmaceutical composition has been formulated, it can be stored in sterile vials as a solution, suspension, gel, emulsion, solid, or dehydrated or lyophilized powder. Such formulations may be stored either in a ready to use form or requiring reconstitution immediately prior to administration. The preferred storage of such formulations is at temperatures at least as low as 4° C. and preferably at −70° C. It is also preferred that such formulations containing the active agents are stored and administered at or near physiological pH. It is presently believed that administration in a formulation at a high pH (i.e. greater than 8) or at a low pH (i.e. less than 5) is undesirable.

The manner of administering the pharmaceutical formulations containing the active agents for systemic delivery can be via intracranial, subcutaneous, intramuscular, intravenous, or oral. Preferably the manner of administration of the formulations containing active agents for local delivery is directly into the brain via intracranial ventricular (icv) with the aid of catheters and pumps.

For oral administration, the pharmaceutical composition of the present invention is encapsulated. The encapsulated active agents can be formulated with or without pharmaceutically-acceptable carriers customarily used in the compounding of solid dosage forms. Preferably, the capsule is designed so that the active portion of the formulation is released at that point in the gastro-intestinal tract when bioavailability is maximized and pre-systemic degradation is minimized. Additional excipients may be included to facilitate absorption of the active agents. Diluents, flavorings, low melting point waxes, vegetable oils, lubricants, suspending agents, tablet disintegrating agents, and binders may also be employed.

Regardless of the manner of administration, the specific dose is calculated according to the approximate body weight of the patient. Other factors in determining the appropriate dosage can include the disease or condition to be treated or prevented, route of administration and the age, sex and medical condition of the patient. In certain embodiments, the dosage and administration is designed to create a preselected concentration range of GDNF in the patient's blood stream. Preferably, GDNF is administered in doses between about 0.0005 mg/kg and 1 mg/kg. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. These dosages may be ascertained through use of the established assays for determining dosages utilized in conjunction with appropriate dose-response data.

As described above, the dosage sufficient to deliver a "therapeutically effective amount" of GDNF can be determined by those of ordinary skill in the art without undue experimentation. A "therapeutically effective amount" may be defined as the amount of GDNF sufficient to inhibit or prevent seizures in the patient.

It should be noted that the GDNF formulations described herein may be used for veterinary as well as human applications and that the term "patient" should not be construed in a limiting manner. In the case of veterinary applications, the dosage ranges should be the same as specified above.

In studies relating to the present invention and described in more detail in the Examples, rhGDNF was shown to prevent kainate induced seizures and the associated neuronal cell loss. This effect was achieved at relatively low doses and in a dose-dependent manner. The pronounced immunostaining for rhGDNF in hippocampal CA1 and CA3 regions coincide with those hippocampal regions that are extremely vulnerable to kainic acid induced toxicity as reported by J. V. Nadler, *The Hippocampus-New Vistas*, p. 463–481 (Alan R. Liss, 1989). The intense immunostaining for rhGDNF by a polyclonal anti-GDNF antibody was achieved bilaterally indicating that this protein can move throughout the ventricular system, which would explain the bilateral preservation of CA1 neurons.

The results indicate that rhGDNF may have both anti-seizure and anti-epileptogenic activity as indicated by the inhibition of the tonic-clonic convulsions and wet dog shakes, respectively. The anti-convulsant properties of rhGDNF appear to be more potent than the anti-epileptogenic actions. Epileptogenesis and seizures appear to have different pharmacologic profiles. Epileptogenesis can be blocked by NMDA receptor antagonists (Stasheff et el., *Science*, 245:648–651 (1989)). In contrast, seizures may require a higher concentration of antagonist or may not be blocked at all by NMDA antagonists, yet may be quite sensitive to commonly used anticonvulsant drugs. Epileptogenesis is a relatively permanent change that occurs when neural tissue is transformed from a normal to an epileptic state (Stasheff et el., supra). In these studies, the effects of rhGDNF were not evaluated directly on these permanent changes in the neural tissue; however, wet dog shakes a prelude to such changes were inhibited by rhGDNF.

Kainic acid induced seizures produces a consistent pattern of brain damage, once status epilepticus has been reached and maintained beyond a critical time period (Ben-Ari, *Neurosci.*, 375–403 (1985); and Tanaka et el., *Prog. Neurobiol.*, 38:317–334 (1992)). The pattern of brain damage observed in these studies is similar to that previously reported in the literature. The lack of kainic acid induced neuronal loss in hippocampal CA3 region has been observed with peripheral kainate administration (Nadler, *The Hippocampus-New Vistas*, p.463–481 (Alan R. Liss, 1989). The neuroprotective effects of rhGDNF upon hippocampal, thalamic and amygdaloid neurons is consistent with a reduction in seizure activity by this neurotrophic factor. However, a possible direct effect of rhGDNF on kainic acid induced excitotoxicity cannot be excluded, since other neurotrophic factors, bFGF and NGF, can protect against glutamate induced excitotoxicity as described by Hefti et el., *Neurobiol. Aging*, 10:515–588 (1989); Berlove et al., *Soc. Neurosci. Abstr.*, 17:1267 (1991); Shigeno et el., *J. Neurosci.*, 11:2914–2919 (1991); Cheng and Mattson, *Neuron*, 7:1031–1041 (1991); Shimohama et al., *Neurosci. Lett.*, 164:55–58 (1993); and Mattson and Cheng, *Stroke*, 24:1–136-1–140 (1993).

However, it is believed that rhGDNF would unlikely act as an inhibitor of glutamaro receptor-channel complexes, based on the structural requirements of these receptors for activation as described in Dingledine et al., *Neurobiology*, 14:1–96 (1988). It is more likely that rhGDNF would influence down stream events or systems that are associated with glutamaro receptor activation. Other neurotrophic factors have been shown to affect the following: (a) changes in glutamaro receptor number or function; (b) induction of protective enzymes either stress proteins or enzymes of superoxide metabolism; (c) alterations in ionic balances-specifically in intracellular calcium stores or $Na^+/K^+$ ATPase activity; and (d) indirect mediator effects via glial cells.

The possibility that rhGDNF may have general depressant activity on synaptic transmission would explain the inhibition of kainic acid induced seizure activity. However, preliminary in vitro electrophysiological studies using rat hippocampal slices indicated that rhGDNF at 2 µg/ml did not affect evoked potentials recorded in areas CA1 and CA3 using standard extracellular recording techniques. The amelioration of kainic acid induced seizures may reflect a reduction in the bioavailability of kainic acid by rhGDNF. This seems unlikely based on the differential dose response relationships for rhGDNF on reducing wet dog shakes and tonic-clonic seizures. Furthermore, inactive rhGDNF did not inhibit kainic acid induced seizures.

The ability of the hippocampus to express GDNF mRNA after kainic acid induced seizures, suggests that the brain may have the capacity to produce GDNF under certain stressful conditions. This phemonoma is not unusual because many members of the NGF gone family are upregulated by excitotoxic lesions and/or seizures. Although not wishing to be bound by any particular theory, it is believed that the local production of GDNF acts as a brake on the seizure/excitotoxic process thus limiting the potential damage that may occur. Hippocampal neurons express both ionotropic and metabotropic glutamate receptors and activation of the ionotropic NMDA receptor indirectly by kainate appears to participate in the regulation of GDNF mRNA. This finding is supported by the recent studies demonstrating that the specific NMDA receptor channel blocker MK-801 (Wong et al., *Proc. Natl Acad. Sci. U.S.A.*, 83:7104–7108 (1986)) attenuated kainic acid induced GDNF mRNA expression (Humpel., *Neurosci.*, 59:791–795 (1994)). This reduction in GDNF mRNA expression is consistent with the above belief, since epileptiform activity would be reduced, less excitotoxic damage would occur, in the CA1 hippocampal region and the stimulus for endogenous GDNF production would be reduced.

The finding that a single bolus intracerebral ventricular injection of rhGDNF reduces the body weights of rats supports previous studies that central or peripheral administration of neurotrophins induce weight loss (Altar et al., *Proc. Natl Acad. Sci. U.S.A.*, 89:11347–11351 (1992); Martin-Iverson et al., *J. Neurosci.*, 14:1262–1270 (1994)). Possible mechanisms underlying the decrease in body weight may be related to alterations in central monoamines such as dopamine and 5-HT.

Peripheral administration of kainic acid also induced body weight changes. Recently, Hajnal et al., *Brain Res. Bull.*, 29:209–916 (1992), demonstrated that the microlesions produced by iontophoretically applied kainic acid into the central nucleus of the amygdala caused body weight loss, hypo- or aphagia and hypo- or adipsia in a dose-dependent manner. These studies also suggested that the lasting feeding disturbances produced by kainic acid to the amygdala were not related causally to the pathological EEG activity changes, but were related to impairment of complex regulatory mechanisms involved in feeding behavior. The amygdala is not the only brain region that controls feeding behavior and the excitotoxicty produced by kainate may affect other brain regions that control feeding behavior. The observation that low doses rhGDNF attenuated kainic acid induced weight loss may be consistent with its ability to reduce excitotoxic damage and to prevent disruption of the neural circuity that is involved in feeding behavior. The accentuation of the weight loss by the highest dose of rhGDNF represents more than the sum of the effects of kainic acid and rhGDNF. Thus, synergy between rhGDNF and other endogenous mediators released during brain injury may be involved in mediating the weight loss phenomena.

Previous in vitro studies indicated that rhGDNF is a potent neurotrophic factor that enhances survival of midbrain dopaminergic neurons and that these effects appeared relatively specific to this transmitter system (Lin et al., Science., 260:1130–1132 (1993)). The present studies indicate that rhGDNF can have additional actions on other neurotransmitter systems such as the glutaminergic system. This indication is further supported by the finding that GDNF mRNA extends to neuronal populations other than dopamine containing neurons (Schaar et al., Exp. Neurol., 124:368–371 (1993); Humpel et al., Neurosci., 59:791–795 (1994).

The use of neurotrophic factors as a potential therapy in epilepsy appears to be a novel approach, and these studies is believed to be the first demonstration of the effective blockade of seizure activity by a neurotrophic factor in a model of temporal lobe epilepsy.

The following examples are intended to illustrate, but not limit, the present invention.

EXAMPLE 1

A. Preparation of Active rhGDNF

Mature rhGDNF was expressed in *E. coli* by the same methods described in McDonald et al., Biochim. Biophys. Acta, 1090:70–80 (1991), incorporated herein by reference. Thereafter, rhGDNF was recovered in the form of inclusion bodies which are isolated from cell lysate by centrifugation and solubilized in 4M guanidine, 90 mM cysteine, 20 mM Tris, pH 8.5. The protein was renatured to the active species by 10X dilution with 0.2M guanidine, 2M urea, 20 mM Tris, pH 8.75. The refold mixture was held at 4° C. for 2 days before being loaded onto an SP Sepharose Big Bead column (Pharmacia) equilibrated in 20 mM sodium acetate, 300 mM sodium chloride pH 5. Recombinant human GDNF was eluted from the column using a salt gradient from 0.3M to 0.6M sodium chloride. Those fractions containing rhGDNF were combined and diluted with an equal volume of 5M sodium chloride, 20 mM sodium citrate before being loaded onto a Phenyl-Sepharose column (High Capacity, Pharmacia), equilibrated in 2.5M sodium chloride, 20 mM sodium citrate, pH 5. The rhGDNF was eluted from high capacity column with a descending salt gradient from 2.5M to 0M sodium chloride. The appropriate fractions are pooled and diluted with an equal volume of 20 mM sodium acetate. The diluted protein mixture was next applied to an SP Sepharose High Performance column (Pharmacia) equilibrated in 20 mM sodium acetate, 475 mM sodium chloride, pH 5. The rhGDNF was eluted from the column with a salt gradient from 475 mM to 675 mM sodium chloride. Fractions containing the purified rhGDNF were combined, concentrated, and stored at −20° C.

B. Preparation of inactive rhGDNF

Recombinant human GDNF was chemically inactivated by blocking the protein's carboxylic acid groups with excess glycine methyl ester via carbodiimide coupling. 100 mgs of purified rhGDNF was diafiltered into 0.5M MES pH 5 at a final protein concentration of 1 mg/ml. EDC and glycine methyl ester were added to 80 and 800 mM, respectively. The reaction was allowed to sit at room temperature for 1 hour. The mixture was dialyzed against phosphate buffered saline to remove excess reagents before being stored at −20° C.

EXAMPLE 2

Surgery

Adult male F344 rats (Harlen) weighing 200–225 g were used. The animals were maintained at a constant temperature (22° C.) and 12 hour light and dark cycle. They were allowed free access to food and water. Animals were anesthetized with 2.5% isoflurane+$O_2$ and positioned in a Kopf stereotaxic frame under continued anesthesia. These animals received a unilateral injection of either rhGDNF (50, 5, 0.5, 0.05 μg/2 μl), vehicle (Phosphate Buffered Saline; 2 μl) or inactive GDNF (2 μg/2 μl) over a 5 minute period into the lateral ventricle (icv) using a 26 gauge Hamilton syringe. The Hamilton syringe was left in place for a further 5 minutes before removal. Injection coordinates relative to bregma were: AP −0.8, ML −1.5, at a depth of 3.5 mm from dura. Animals had their skin sutured with wound clips and were allowed to recover. Either rhGDNF, inactive GDNF or vehicle were given 1 hr before kainic acid. Kainic acid (Tocris Neuramin, England..) Twelve mg/kg was dissolved in 0.9% saline and was administered subcutaneously. Animal weights were recorded daily for the duration of the study,

EXAMPLE 3

Brain Histology

Seven days after KA administration, the rats were anesthetized with sodium pentobarbitone 55 mg/kg (i.p.) and transcardially perfused with phosphate buffered formalin solution. The brains were removed and immersion-fixed for at least 24 hr in the same fixative. The brains were then dehydrated, embedded in paraffin wax and cut coronally in 5-μm-thick slices and sections were Nissl stained. Using a Leitz microscope, viable cell counts were performed bilaterally in the CA1 and CA3 regions of the hippocampus, thalamus (parafascicular thalamic and periventricular thalamic nuclei) and amdydala (amygdalohippocampal area, anterolateral; basomedial amygdaloid nucleus, posterior; basolateral amygdaloid nucleus, posterior and postermedial cortical amygdaloid nucleus). Counts, lengths and areas were performed at Bregma −4.16 mm (Paxinos and Watson). The total linear length of the hippocampal CA1 sector was measured by means of the Image-1 (Universal Imaging Corp., West Chester, Pa.) image analysis system. The area of the thalamic and amygdaloid areas were measured by means of a 100 mm$^2$ eye piece graticule corresponding to 0.25 mm$^2$ on a linear calibrated scale using a 20x objective. Cell counts were expressed as cells/mm for the hippocampal region and cells/mm$^2$ for the thalamus and amdydala.

EXAMPLE 4

Distribution of rhGDNF

Twenty-four hours after intracranial ventricular (icv) injection of rhGDNF (100 µg/4 µl), the rats were perfused with 10% neutral buffered formalin, brains removed, paraffin embedded and sectioned at 5 microns onto charged slides. Sections were immunostained for GDNF using an affinity-purified rabbit antibody to rhGDNF. The antibody (0.59 mg/ml) was used at a 1:100 dilution and incubated with the sections for 1 hour prior to applying monovalent biotinylated anti-rabbit and subsequently, Omnitags Streptavidin Alkaline Phosphatase (Lipshaw Immunon, Pittsburgh, Pa.). The sections were developed using the New Fuchsin Substrate System (Dako Corp., Carpinteria, Calif.). Negative controls included, sections in which irrelevant antibody at similar concentrations was substituted for the primary antibody and sections from phosphate buffered saline injected rats. Slides were mounted with Crystal Mount (Biomeda, Foster City, Calif.) and later, Permount (Fischer Scientific, Fairlawn, N.J.) to create a permanent preparation. Distribution of rhGDNF was evaluated using a Leitz microscope equipped with an ocular micrometer.

EXAMPLE 5

Bioassay

Bioassay for rhGDNF and inactive GDNF activity was performed as described by Lin et al., *J. Biol. Chem.*, 265:8942–8947 (1990), incorporated herein by reference. Briefly, the in vitro assay for GDNF activity measures the survival of chick embryo sympathetic chain (E9) neurons. Two thousand purified neurons were placed into each well of a 96-well dish and serial dilutions of GDNF samples were added. After 44 hours, neuronal survival was estimated by the ability of live cells to reduce the vital dye MTT (3–4[, 5-dimethylthiazol-2-yl]-2,5-diphenyltetrazolium) (Sigma Chemical Co., St. Louis, Mo.). The bioactivity of rhGDNF was expressed as an EC$_{50}$ value, a dilution of rhGDNF that gave 50% of the maximal neuronal survival based on the MTT assay.

EXAMPLE 6

Statistics

Histological comparisons between control and GDNF treated animals were analyzed using students t-test. Logistic regression was performed to test for a dose-response effect due to rhGDNF on wet dog shakes and tonic-clonic seizures, followed by a Fisher exact test. Body weight comparisons were analyzed using Wald test, one way analysis of variance (ANOVA) followed by a Scheffe multiple comparison procedure.

EXAMPLE 7

Results

Peripheral injection of 12 mg/kg kainate to Fischer 344 rats induced wet dog shakes and seizures within two hours and mortality within the first 8 hours (Table 1).

TABLE 1

| GDNFµ/2 µL | Wet dog shakes | Tonic-clinic seizures | Death |
|---|---|---|---|
| 50 | 2/10 | 0/10 | 0/10 |
| 5 | 5/8 | 1/8 | 0/8 |
| 0.5 | 7/7 | 0/7 | 0/7 |
| 0.05 | 8/8 | 7/8 | 4/8 |
| 2, inactive | 8/8 | 7/8 | 4/8 |
| Vehicle | 13/13 | 13/13 | 2/13 |

Table 1 shows the anti-convulsant activity of rhGDNF against kainic acid (12 mg/kg s.c.). Recombinant human GDNF, vehicle or inactive GDNF were given (icv) 1 hour before kainic acid. The values indicate the number of rats that had wet dog shakes, tonic-clonic seizures or died. All animals were monitored for the first 12 hours after administration of kainic acid and then on a daily basis. Using Fisher's exact test, the dose levels that were significant for wet dog shakes were 50 µg (p=0.00009) and 5 µg (p=0.042). For tonic-clonic seizures doses 0.05 (p=0.012), 0.5 (p=0.00001), 5 (p=0.00007) and 50(p=0.0000009) were significant.

These behavioral changes as reported in Table 1 were consistent with previous studies reported in Lothman & Collins, *Brain Res.*, 218:299–318 (1981). Intraventricular rhGDNF (0.05–50 µg/2 µg) significantly (p=0.0036) attenuated kainic acid induced wet dog shakes in a dose-dependent manner. Similarly, kainic acid treated rats that received rhGDNF by the intracerebroventricular route at doses between (0.5–50 µg/2 µl) did not exhibit tonic-clonic seizure activity, whereas 50% of the animals at the low dose rhGDNF (0.05 µg/2 µl), and all animals injected with either vehicle (PBS n=13) or inactive GDNF (2 µg/2 µl), had tonic-clonic seizures (p=0.0008, logistic regression analysis; see Table 1). No deaths occurred in rats receiving rhGDNF whereas deaths occurred in rats receiving vehicle or inactive GDNF. Furthermore, rhGDNF delayed the onset of wet dog shakes. Vehicle treated animals displayed wet dog shakes within 30 minutes post kainic acid administration. Recombinant human GDNF (50 and 5 µg/2 µl) delayed the onset of wet dog shakes by a further 30–60 minutes, whereas the lower doses delayed the onset by only 15–20 minutes.

Figure 1B:
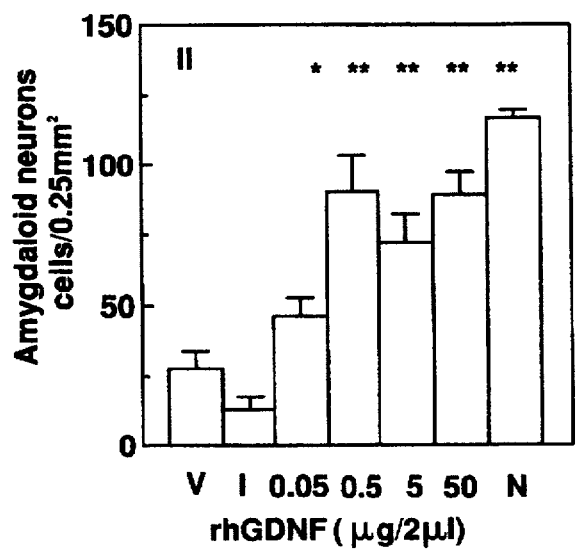
Figure 1C:
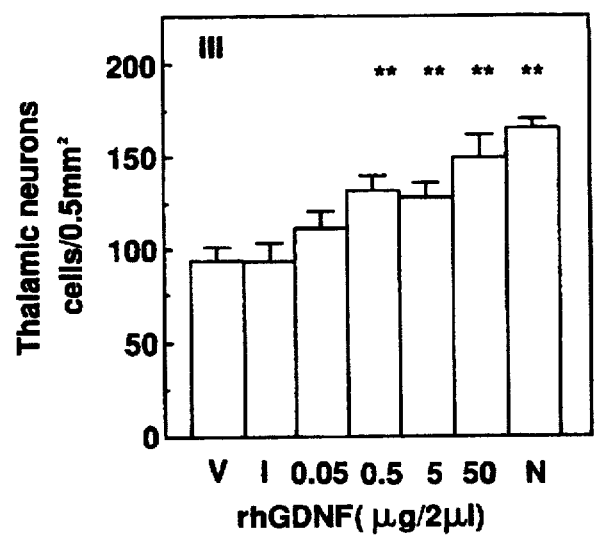
Figure 2A:
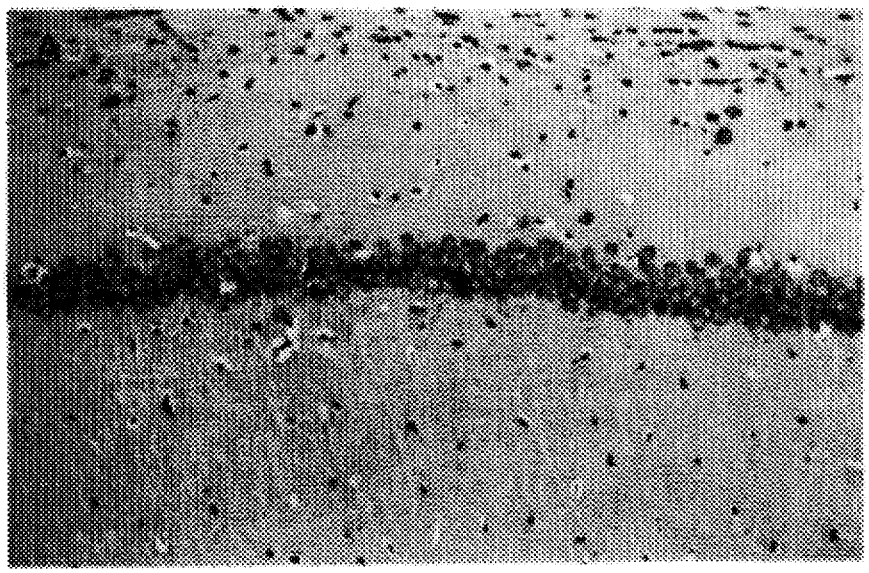
FIGS. 2A–2C shows that rhGDNF protects against kainic acid induced hippocampal CA1 pyramidal cell loss. Coronal sections of the rat CA1 hippocampal region stained with cresyl violet×25.
Figure 2B:
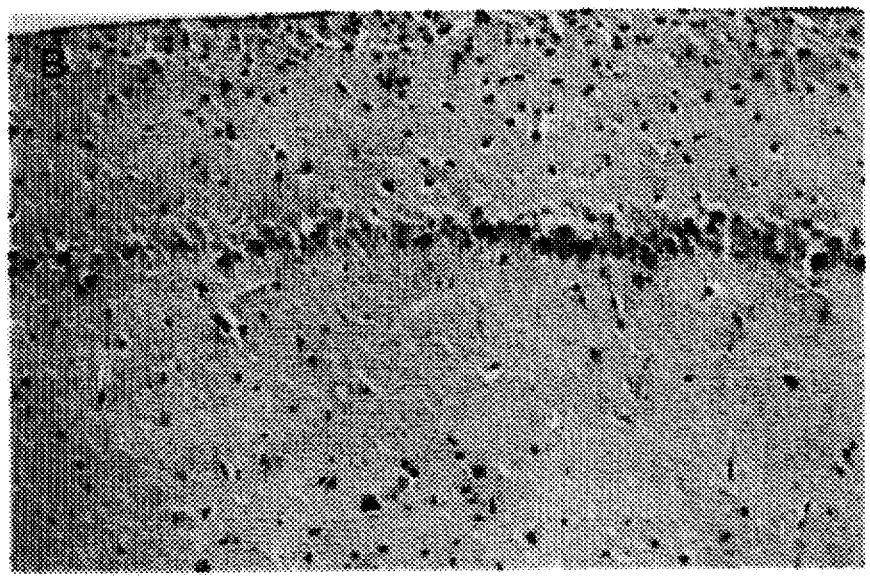
Figure 2C:
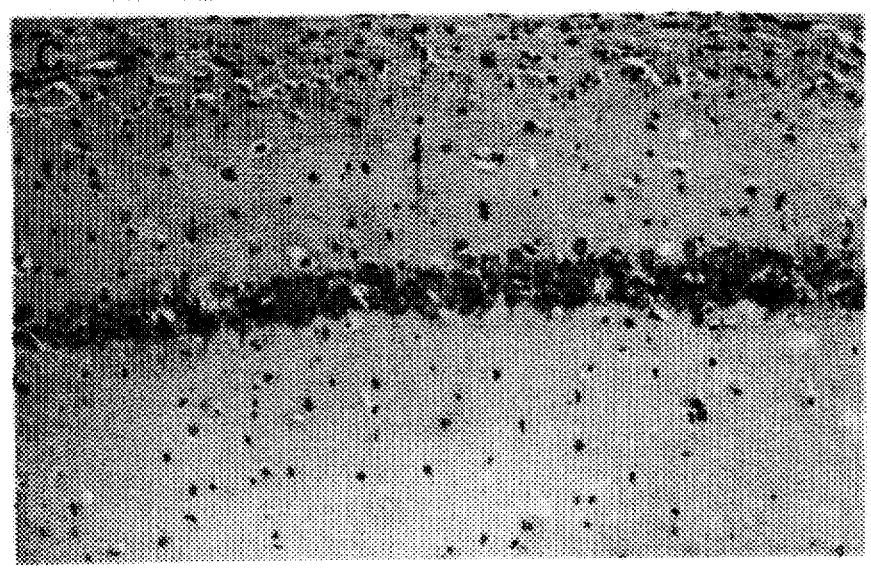

Peripheral injection of kainate consistently produced selective hippocampal CA1, thalamic, and amygdala neuronal loss that was detected seven days later. Histological examination of the hippocampus revealed a 50–60% loss of CA1 pyramidal cells in all animals that received vehicle or inactive GDNF (icv) compared to normal control animals (FIGS. 1 and 2). The loss of CA1 pyramidal cells by kainate was highly significant (p<0.01, students t-test). Administration of rhGDNF (0.5–50 µg/2 µl, icv) significantly (p<0.001) attenuated the extensive CA1 pyramidal cell loss induced by kainate in both left and right hippocampi compared to the vehicle (2 µl icv), low dose GDNF (0.05 µg/2 µl) or inactive GDNF (2 µg/2 µl) treated animals. The number of viable CA1 pyramidal cells was not significantly different in the rhGDNF (50 µg) treated compared to normal animals (FIG. 1). Kainate acid also caused extensive thalamic and amygdaloid neuronal loss which was significantly (p<0.01) attenuated by rhGDNF (0.5–50 µg/µl) (FIG. 1).

Protection by rhGDNF (50 µg/2 µl) was also shown against kainic acid induced neuronal cell loss by inhibiting the extensive necrosis and vacuolization of the thalamic formation by kainic acid without rhGDNF.

Immunostained sections of rhGDNF (100 µg/4 µl) injected rats revealed widespread distribution of the protein throughout the ventricular system, periventricular tissues, subarachnoid space and subjacent neuropil at 24 hours after the injection of rhGDNF. Positive immunostaining was present at the lateral aspect of the hippocampus in areas CA1b, CA1c, CA2 and CA3 which are adjacent to the posterior portions of the lateral ventricles.

Figure 3:
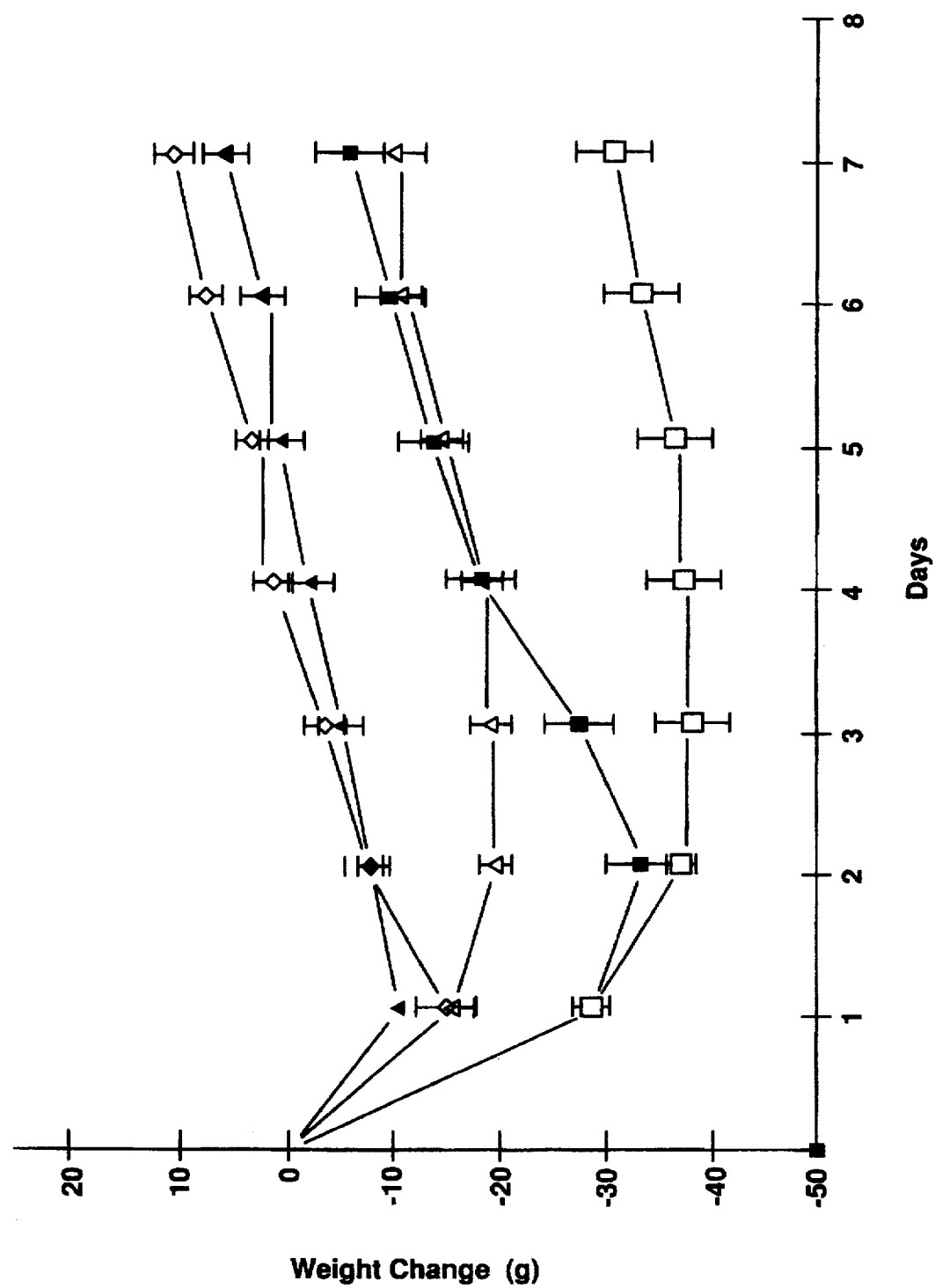
FIG. 3 graphs the effects of △ rhGDNF (50 μg/2 μl icv), ▲ vehicle (2 μl icv), □ kainic acid (12 mg/kg s.c.)+rhGDNF (50 μg/2 μl, icv), ◇ kainic acid (12 mg/kg s.c.)+rhGDNF (0.5 μg/2 μl icv) and ■ kainic acid (12 mg/kg s.c.)+vehicle (2 μl, icv), on mediating weight loss. Body weights were measured daily for seven days and values are expressed as body weight change from day zero. Compounds were administered on day zero. Values are mean±S.E.M., (n=7–11).

Administration of rhGDNF (50 µg/2 µl) icv to naive animals produced a large decrease in body weight and a slower rate of body weight increase over the study duration compared to vehicle treated animals (FIG. 3). The analysis showed both a difference in the rate of body weight change from day zero to day seven (Wald test p<0.001), and a difference in the total weight change (Wald test p<0.001). The change from baseline to day 7 in body weight between kainate and rhGDNF dose groups, as well as the kainate and vehicle group were compared (one-way ANOVA). The analysis revealed a clear difference between the weight change among the treatment groups (p<0.001). Lower doses of rhGDNF appear to attenuate the weight loss caused by kainate while producing no additional weight loss themselves (Scheffe test p<0.05). However, the addition of higher doses of rhGDNF (50 and 5 µg/µl) appear to exacerebate weight loss (Scheffe test p<0.05) (Table 2).

TABLE 2

| Group | Mean | SD |
|---|---|---|
| 50 µg rhGDNF | −10.6 | 6.8 |
| Vehicle | 5.4 | 4.8 |
| KA + Vehicle | −6.5 | 9.0 |
| KA + 0.05 µg rhGDNF | 4.3 | 6.4 |
| KA + 0.5 µg rhGDNF | 10.1 | 4.7 |
| KA + 5 µg rhGDNF | −15.9 | 22.1 |
| KA + 50µ rhGDNF | −31.4 | 11.9 |

Highly-purified rhGDNF promoted the survival in culture of chick sympathetic chain neurons. The chick embryo sympathetic chain neuronal survival assay on the chemically modified rhGDNF (up to 750 ng/ml) showed no detectable biological activity when compared to the active rhGDNF ($EC_{50}$ 10 ng/ml).

The inactive and active forms of GDNF were tested for lipopolysaccharide (LPS) and *E. coli* protein (ECP) levels. These levels were >1 EU/mg and >50 ppm respectively.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A method for inhibiting seizure activity and neuronal cell loss resulting from seizure activity, comprising the intracranial, intraventricular or intrathecal administration of an effective amount of glial cell line-derived neurotrophic factor to inhibit said seizure activity, wherein said neurotrophic factor comprises an amino acid sequence of human (SEQ ID NO:1) or rat (SEQ ID NO:2) glial cell line-derived neurotrophic factor or an amino acid sequence which is in excess of 70% identical to human or rat glial cell line-derived neurotrophic factor.

2. The method of claim 1, wherein said seizure activity is related to epilepsy.

3. The method of claim 1, wherein said glial cell line-derived neurotrophic factor is produced by recombinant DNA methods.

4. The method of claim 1, wherein said seizure activity is caused by a deleterious amount of kainic acid.

5. The method of claim 1, wherein said glial cell line-derived neurotrophic factor is administered in a pharmaceutically acceptable carrier.

6. The method of claim 1, wherein said glial cell line-derived neurotrophic factor is administered intracranially.

7. A method for inhibiting seizure activity and neuronal cell loss resulting from seizure activity, comprising the intracranial, intraventricular or intrathecal administration of an effective amount of human glial cell line-derived neurotrophic factor sufficient to inhibit said seizure activity, wherein said neurotrophic factor comprises the amino acid sequence (SEQ ID NO:1);

| Ser | Pro | Asp | Lys | Gln | Met | Ala | Val | Leu | Pro | Arg | Arg | Glu | Arg | Asn |
|-----|-----|-----|-----|-----|-----|-----|-----|-----|-----|-----|-----|-----|-----|-----|
| Arg | Gln | Ala | Ala | Ala | Ala | Asn | Pro | Glu | Asn | Ser | Arg | Gly | Lys | Gly |
| Arg | Arg | Gly | Gln | Arg | Gly | Lys | Asn | Arg | Gly | Cys | Val | Leu | Thr | Ala |
| Ile | His | Leu | Asn | Val | Thr | Asp | Leu | Gly | Leu | Gly | Tyr | Glu | Thr | Lys |
| Glu | Glu | Leu | Ile | Phe | Arg | Tyr | Cys | Ser | Gly | Ser | Cys | Asp | Ala | Ala |
| Glu | Thr | Thr | Tyr | Asp | Lys | Ile | Leu | Lys | Asn | Leu | Ser | Arg | Asn | Arg |
| Arg | Leu | Val | Ser | Asp | Lys | Val | Gly | Gln | Ala | Cys | Cys | Arg | Pro | Ile |
| Ala | Phe | Asp | Asp | Asp | Leu | Ser | Phe | Leu | Asp | Asp | Asn | Leu | Val | Tyr |
| His | Ile | Leu | Arg | Lys | His | Ser | Ala | Lys | Arg | Cys | Gly | Cys | Ile. | |

8. The method of claim 7, wherein said seizure activity is related to epilepsy.

9. The method of claim 7, wherein said glial cell line-derived neurotrophic factor is produced by recombinant DNA methods.

10. The method of claim 7, wherein said seizure activity is caused by a deleterious amount of kainic acid.

11. The method of claim 7, wherein said glial cell line-derived neurotrophic factor is administered in a pharmaceutically acceptable carrier.

* * * * *

UNITED STATES PATENT AND TRADEMARK OFFICE
CERTIFICATE OF CORRECTION

PATENT NO. : 5,733,875
DATED : March 31, 1998
INVENTOR(S) : David Martin

It is certified that error appears in the above-identified patent and that said Letters Patent is hereby corrected as shown below:

Column 1,
Line 27, change "14:3413-1325" to -- 14:3413-3425 --.

Column 4,
Line 45, add -- and rat GDNF which has the amino acid sequence:
Ser Pro Asp Lys Gln Ala Ala Ala Leu Pro Arg Arg Glu Arg Asn
Arg Gln Ala Ala Ala Ala Ser Pro Glu Asn Ser Arg Gly Lys Gly
Arg Arg Gly Gln Arg Gly Lys Asn Arg Gly Cys Val Leu Thr Ala
Ile His Leu Asn Val Thr Asp Leu Gly Leu Gly Tyr Glu Thr Lys
Glu Glu Leu Ile Phe Arg Tyr Cys Ser Gly Ser Cys Glu Ala Ala
Glu Thr Met Tyr Asp Lys Ile Leu Lys Asn Leu Ser Arg Ser Arg
Arg Leu Thr Ser Asp Lys Val Gly Gln Ala Cys Cys Arg Pro Val
Ala Phe Asp Asp Asp Leu Ser Phe Leu Asp Asp Ser Leu Val Tyr
His Ile Leu Arg Lys His Ser Ala Lys Arg Cys Gly Cys Ile Column 6,
Line 24, after "intracranial," add -- intrathecal --.

Column 8,
Line 9, change "glutamaro" to -- glutamate --.
Line 11, change "glutamaro" to -- glutamate --.
Line 35, change "gone" to -- gene --.

Column 11,
Line 1, change "amdydala" to -- amygdala --.
Line 14, change "amdydala" to -- amygdala --.

UNITED STATES PATENT AND TRADEMARK OFFICE
CERTIFICATE OF CORRECTION

PATENT NO. : 5,733,875
DATED : March 31, 1998
INVENTOR(S) : David Martin

It is certified that error appears in the above-identified patent and that said Letters Patent is hereby corrected as shown below:

Column 12,
Line 18, change "Tonic-clinic seizures" to -- Tonic-clonic seizures --.

Signed and Sealed this

Eighteenth Day of June, 2002

*Attest:*

JAMES E. ROGAN
*Attesting Officer*    *Director of the United States Patent and Trademark Office*